United States Patent [19]

Sweeney

[11] Patent Number: 5,059,733

[45] Date of Patent: Oct. 22, 1991

[54] PROCESS FOR MAKING 1-HEXENE AND HIGH OCTANE BLENDING COMPONENTS

[75] Inventor: William A. Sweeney, Larkspur, Calif.

[73] Assignee: Chevron Research and Technology Company, San Francisco, Calif.

[21] Appl. No.: 542,298

[22] Filed: Jun. 22, 1990

[51] Int. Cl.$^5$ ................................................ C07C 1/00
[52] U.S. Cl. ................................. 585/324; 585/510; 585/520; 585/639; 585/643; 585/644; 585/648; 585/653
[58] Field of Search ............... 585/324, 328, 639, 640, 585/648, 510, 520, 643, 644, 653; 568/697

[56] References Cited

U.S. PATENT DOCUMENTS

| | | | |
|---|---|---|---|
| 3,283,027 | 11/1966 | Lundeen et al. | 260/682 |
| 3,482,952 | 12/1969 | Sieg et al. | 568/697 |
| 3,600,455 | 8/1971 | Dean | 260/682 |
| 4,234,752 | 11/1980 | Wa et al. | 585/640 |
| 4,270,015 | 5/1981 | Knifton | 585/639 |
| 4,283,305 | 8/1981 | Chauvin et al. | 252/431 |
| 4,316,851 | 2/1982 | Le Pennec et al. | 260/408 |
| 4,366,087 | 12/1982 | Le Pennec et al. | 252/431 |
| 4,398,049 | 8/1983 | Le Pennec et al. | 585/512 |
| 4,490,567 | 12/1984 | Drake | 585/324 |
| 4,827,046 | 5/1989 | Harandi et al. | 568/697 |

FOREIGN PATENT DOCUMENTS

| | | |
|---|---|---|
| 0222356 | 5/1987 | European Pat. Off. . |
| 0150832 | 11/1988 | European Pat. Off. . |
| 1233020 | 5/1971 | United Kingdom . |

OTHER PUBLICATIONS

Lundeen et al., *JORG Chem.*, vol. 32, 1967, pp. 3386–3389.
Davis, *American Chemical Society*, vol. 18, No. 3, 1979, pp. 191–198.
Che et al., *Elsevier Science Publishers B.V.*, Amsterdam, 1985, pp. 309–318.

*Primary Examiner*—Curtis R. Davis
*Attorney, Agent, or Firm*—Richard J. Sheridan; Tom G. DeJonghe

[57] ABSTRACT

Disclosed is a process for preparing n-hexenes and high octane blending components from a mixture of $C_6$ olefin isomers. Also disclosed is a process for preparing 1-hexene from a mixture of $C_6$ olefin isomers which provides high octane blending components as a by-product.

16 Claims, No Drawings

PROCESS FOR MAKING 1-HEXENE AND HIGH OCTANE BLENDING COMPONENTS

BACKGROUND OF THE INVENTION

1. Field of the Invention

The present invention relates to a method for producing 1-hexene and high octane blending components from a mixture of $C_6$ olefin isomers.

2. Description of the Prior Art

Compounds having a terminal double bond (hereinafter referred to as "terminal olefins" or "α-olefins") are very useful industrially as raw materials for heat-resistant polymers, comonomers for the production of polyolefins, starting materials for detergents and so forth. The terminal olefin 1-hexene is especially valuable for many uses such as dimerization to dodecenes which are suitable for making biodegradable detergents, using it as a feed for the OXO reaction to make relatively linear $C_7$ alcohols, and as a comonomer in making linear low density polyethylene.

A potential source of 1-hexene is a mixture of n-hexenes which contains 1-hexene, cis and trans 2-hexene, and cis and trans 3-hexene. Unfortunately, however, the amount of 1-hexene in these mixtures is normally very low. For example, thermodynamic equilibration of n-hexenes produces a mixture containing only about 2–4% 1-hexene. While it is possible to separate the 1-hexene from the other n-hexenes in these mixtures, due to the very low levels of 1-hexene such a procedure would be uneconomical. Thus, there exists a need for a method by which the amount of 1-hexene in these n-hexene mixtures can be substantially increased.

A known method for producing terminal olefins, such as 1-hexene, is to dehydrate a 2-alcohol, i.e., a compound of the formula

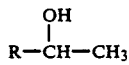

where R is a hydrocarbyl group. For example, U.S. Pat. No. 3,283,027, issued Nov. 1, 1966 to Lundeen et al, discloses the dehydration of 2-alcohols to terminal olefins using a catalyst which is a thorium, scandium, yttrium or rare earth oxide. While this dehydration reaction can produce an α-olefin and/or a 2-olefin, the Lundeen et al. product is said to be 90% or more α-olefin.

U.S. Pat. No. 3,600,455, issued Aug. 17, 1971 to Dean, discloses a process for producing the terminal olefin 4-methylpentene-1 by dehydrating 4-methylpentanol-1 or 4-methylpentanol-2 by passing it over an alkalized alumina catalyst.

U.S. Pat. No. 4,234,752, issued Nov. 18, 1980 to Wu et al., discloses the dehydration of $C_{2-20}$ alcohols in the presence of gamma-alumina (which may be base-treated) employing an inert carrier gas to produce an olefin. The process is said to minimize isomerization which can convert desired products to undesired products. For example, according to Wu et al., 3-methyl-1-butanol can be dehydrated by this process to produce 3-methyl-1-butene having a 7.7 wt. % purity.

U.S. Pat. No. 4,490,567, issued Dec. 25, 1984 to Drake, discloses a process for the selective dehydration of 2-alcohols to α-olefins using a catalyst which is (1) at least one catalytic metal oxide on a low surface area aluminum oxide-containing support, or (2) a mixture of thorium oxide and cerium oxide on a base-treated aluminum oxide-containing support. Also described is a process for obtaining high purity 4-methyl-1-pentene by the dehydration of 4-methyl-2-pentanol followed by disproportionation with ethylene.

European Patent Specification Publication No. 0150832, published Nov. 2, 1988, discloses a process for preparing α-olefins by dehydrating 2-alcohols using a high purity (i.e., substantially free of silicon and titanium) zirconium oxide catalyst, and European Patent Specification Publication No. 0222356, published May 20, 1987, discloses the dehydration of 2-alcohols to α-olefins using a zirconia catalyst which has been treated with an alkaline solution.

Lundeen and Hoozer, "Selective Catalytic Dehydration. Thoria-Catalyzed Dehydration of Alcohols", J. Org, Chem., 32, pp. 3386–3389 (1967) discloses that the thoria-catalyzed dehydration of secondary 2-alcohols is selective for α-olefins, and that the amount of ketone by-product is low, and Davis, "Catalytic Conversion of Alcohols. 11. Influence of Preparation and Pretreatment on the Selectivity of Zirconia", Ind. Eng. Chem. Prod. Res. Dev., Vol. 18, No. 3, pp. 181–198 (1979) discloses that a zirconia catalyst is similar to thoria for both the dehydration and α-olefin selectivity in the conversion of 2-alcohols to olefins.

Other methods of preparing α-olefins are also known. For example, British Patent Specification No. 1,233,020, published May 26, 1971, discloses a method for making 4-methylpentene-1 by subjecting a mixture of acetone and isobutyraldehyde to conditions under which acetone undergoes condensation both with itself to form diacetone alcohol and with isobutyraldehyde to form the acetone/isobutyraldehyde condensate methyl, 2-methyl 3-hydroxy butyl ketone, subjecting the mixed condensates to conditions under which they undergo dehydration to the corresponding olefinically unsaturated ketones, hydrogenating these ketones to saturated alcohols and dehydrating these saturated alcohols over alkalized alumina to form a mixture of 4-methylpentenes-1 and -2 and a mixture of methyl hexenes.

A process for producing 1-hexene has now been discovered which not only provides 1-hexene in useful quantities, but also produces a useful, valuable ether by-product.

SUMMARY OF THE INVENTION

In accordance with the present invention, there is provided a process for the production of n-hexenes and high octane blending components comprising reacting a mixture of $C_6$ olefin isomers comprising (1) n-hexenes and (2) reactive $C_6$ iso-olefins with an alcohol in the presence of an acid catalyst until the reactive $C_6$ iso-olefins are etherified. If desired, the etherified iso-olefins may then be separated from the reaction product.

There is also provided in accordance with the present invention, a process for making 1-hexene comprising:

A. reacting a mixture of $C_6$ olefin isomers comprising (1) n-hexenes and (2) reactive $C_6$ iso-olefins with an alcohol in the presence of an acid catalyst until the reactive $C_6$ iso-olefins are etherified;

B. separating the etherified $C_6$ iso-olefins from the product of step A;

C. reacting the remainder of the product of step A with an electrophilic compound containing reactive hydrogen under conditions which permit the electrophilic compound containing reactive hydrogen to add to carbon-carbon double bonds; and D. cracking the product of step C to produce a mixture of $C_6$ olefins containing a quantity of 1-hexene greater than that in the mixture of $C_6$ olefin isomers employed in step A.

In accordance with the present invention, there is also provided a process for making 1-hexene comprising:
A. reacting a mixture of $C_6$ olefin isomers comprising (1) n-hexenes and (2) reactive $C_6$ iso-olefins with an alcohol in the presence of an acid catalyst until the reactive $C_6$ iso-olefins are etherified;
B. separating the etherified iso-olefins from the product of step A;
C. reacting the remainder of the product of step A with an electrophilic compound containing reactive hydrogen under conditions which permit said electrophilic compound to add to carbon-carbon double bonds, said electrophilic compound being hydrolyzable to an alcohol after addition to the carbon-carbon double bond;
D. hydrolyzing the product of step C to produce of mixture of $C_6$ alcohols; and
E. cracking the product of step D to produce a mixture of $C_6$ olefins containing a quantity of 1-hexene greater than that in the mixture of $C_6$ olefin isomers employed in step A.

The present invention further provides a process for making 1-hexene comprising:
A. reacting a mixture of $C_6$ olefin isomers comprising (1) n-hexenes and (2) reactive $C_6$ iso-olefins with an alcohol in the presence of an acid catalyst until the reactive $C_6$ iso-olefins are etherified;
B. separating the etherified iso-olefins from the product of step A;
C. reacting the remainder of the product of step A with an electrophilic reactant selected from the group consisting of water and a hydrolyzable electrophilic compound containing reactive hydrogen under conditions which permit said electrophilic reactant to add to carbon-carbon double bonds;
D. when the electrophilic reactant employed in step C is a hydrolyzable electrophilic compound containing reactive hydrogen, hydrolyzing the product of step C to form alcohols;
E. converting the alcohols produced to alkyl xanthates; and
F. cracking the product of step E to produce a mixture of $C_6$ olefins containing a quantity of 1-hexene greater than that in the mixture of $C_6$ olefin isomers employed in step A.

DETAILED DESCRIPTION OF PREFERRED EMBODIMENTS

The starting material employed in the processes of the present invention is a mixture of $C_6$ olefin isomers comprising n-hexenes and reactive $C_6$ iso-olefins. As used herein, the term "reactive $C_6$ iso-olefin" refers to olefins having six carbon atoms and a branch at the double bond. These reactive $C_6$ iso-olefins have the general formula

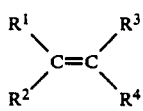

where $R^1$ and $R^2$ are both $C_1$ and $C_3$ alkyl groups and the sum of the carbon atoms in groups $R_1$ and $R_2$ does not exceed four, and $R^3$ and $R^4$ are either hydrogen or alkyl groups. When either or both of $R_3$ and $R_4$ is alkyl, the sum of the carbon atoms in $R_1$, $R_2$, $R_3$ and $R_4$ does not exceed four. Examples of these reactive $C_6$ iso-olefins include the following:

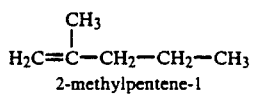
2-methylpentene-1

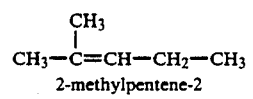
2-methylpentene-2

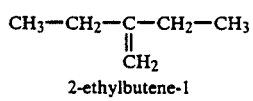
2-ethylbutene-1

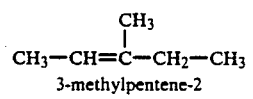
3-methylpentene-2

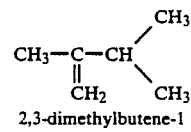
2,3-dimethylbutene-1

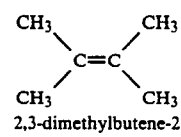
2,3-dimethylbutene-2

These compounds are termed "reactive" herein because they can readily react with an alcohol to form an ether.

The starting material employed in the processes of this invention may also contain unreactive $C_6$ iso-olefins. As used herein, the term "unreactive $C_6$ iso-olefins" refers to olefins having six carbon atoms and a branch which is not at the double bond. They are termed "unreactive" because they do not readily react with an alcohol in the presence of an acid catalyst to form an ether. Examples of these unreactive $C_6$ iso-olefins include the following:

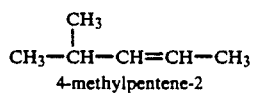
4-methylpentene-2

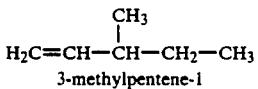
3-methylpentene-1

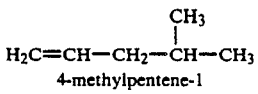
4-methylpentene-1

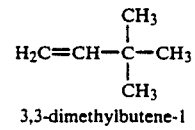
3,3-dimethylbutene-1

The terms "reactive $C_6$ iso-olefin" and "unreactive $C_6$ iso-olefin" both include cis and trans isomers, where applicable.

The source of the starting mixture is not critical. It could come from various cracking operations such as fluid catalytic cracking or steam cracking. A convenient source is the mixture of propylene dimers made by metal-catalyzed processes such as those described in Chem. Rev. 1986, p. 353. Particularly suitable are the nickel catalyzed processes such as the Dimersol process. This process was developed by Institut Francaise du Petrole and involves the catalyzed, liquid phase dimerization of propylene.

The Dimersol process is described in Benedek et al., Oil & Gas Journal, Apr. 28, 1980, pp. 77-83, which is incorporated by reference herein in its entirety. The process is also generally described in U.S. Pat. No. 4,283,305 (issued Aug. 11, 1981 to Chauvin et al.); U.S. Pat. No. 4,316,851 (issued Feb. 23, 1982 to Le Pennec et al.); U.S. Pat. No. 4,366,087 (issued Dec. 28, 1982 to Le Pennec et al.); and U.S. Pat. No. 4,398,049 (issued Aug. 9, 1983 to Le Pennec et al.), each of which is incorporated by reference herein in its entirety.

The product of the dimerization of propylene by the Dimersol process is often referred to as "Dimate" and, as disclosed in the aforementioned Benedek et al. article, contains high octane isohexenes and small quantities of trimers and higher molecular weight olefins. The product contains 1-, 2- and 3-hexene; 2-methylpentene-2; 4-methylpentene-2 and 2,3-dimethylbutene-2. If desired, the 4-methylpentene-2 (an unreactive $C_6$ iso-olefin) may be separated from the Dimate product by distillation prior to its use in the process of the present invention.

The starting mixture, which comprises n-hexenes and reactive $C_6$ iso-olefins, is reacted with an alcohol in the presence of an acid catalyst. This causes a reaction between the reactive $C_6$ iso-olefins (but not the unreactive $C_6$ iso-olefins) and the alcohol to form ethers having the structure

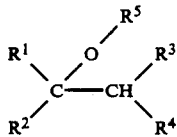

where $R^1$, $R_2$, $R^3$ and $R^4$ are as defined above, and together represent the remainder of the reactive $C_6$ iso-olefin and $R^5$ is the remainder of the alcohol. The other components of the starting mixtures, including the n-hexenes and any unreactive $C_6$ iso-olefins which may have been present in the starting material, do not react with the alcohol. If desired, the unreactive $C_6$ iso-olefins can be made to react with the alcohol by including an olefin isomerization catalyst in the reaction system.

It is believed that acid catalysts suitable for use in the etherification reaction are known in the art. They include sulfonated ion exchange resins such as those sold under the designation Amberlyst, sulfuric acid and toluene sulfonic acids. It is likewise believed that suitable reaction conditions for this etherification step are known in the art. Since it is desirable to drive the etherification as far to completion as possible, the use of catalytic distillation techniques, such as those described below, is preferred.

The alcohols which may be used in the practice of this invention are any organic compound which contains a —OH group and does not contain other moieties which will interfere with the etherification reaction. These alcohols can, for instance, contain both a —OH group and a —COOH group and be suitable for use in this invention. Generally, however, $C_1$-$C_6$ aliphatic alcohols are employed because of their availability. Specific examples of alcohols useful in the practice of the present invention include methanol, ethanol, isopropanol and 1-butanol.

The etherification of the reactive $C_6$ iso-olefins should be conducted in a manner which causes the etherification reaction to achieve a high conversion of the reactive iso-olefins to ethers. A particularly preferred method of achieving high conversion is catalytic distillation, which involves a combination of the ether formation reaction with distillation in such a way that the reactants (the $C_6$ olefin isomers and the alcohol) are refluxed over the acidic catalyst while the product ethers are removed from the catalyst by passing to the bottom of a distillation fractionation zone. Fractionation and catalysis may occur in the same zone, or the catalysis zone may be placed above the fractionation zone. This catalytic distillation may be conducted in either a batch or continuous fashion.

Catalytic distillation is preferred in the practice of the present invention because it causes the etherification reaction to go to high conversion. With iso-olefins containing fewer than six carbon atoms, e.g., isobutene and isoamylene, high conversion to ether can be obtained without using a catalytic distillation process. However, with $C_6$ iso-olefins, particularly the 2,3-dimethylbutenes, the equilibrium for ether formation is less favorable and catalytic distillation becomes desirable.

In general, the conditions for catalytic distillation are as follows:

1. Temperature from about 40° C. to about 180° C.
2. Pressure, which is appropriate to the temperature, from about atmospheric to about 300 psi.
3. Reaction time required, which depends on temperature and catalyst chosen, may range from about a minute to several days.
4. The catalyst should be a moderately strong, solid acidic catalyst such as Amberlyst 15. The amount present in a batch reaction will range from about 0.1 to about 20% by weight of the reactive $C_6$ iso-olefins present. In a continuous reaction, the space velocity will range from about 0.01 to about 100 grams of reactive $C_6$ iso-olefin per gram of catalyst per hour.

The whole product of this etherification reaction can be used to prepare high-octane gasoline. Preferably, however, the etherified iso-olefins are separated from the reaction product by, e.g., distillation. These etherified iso-olefins are particularly suitable as a high octane blending component for gasoline. The remainder of the reaction product, which comprises n-hexenes (and possibly other $C_6$ olefins) may then be further processed in accordance with the present invention to produce 1-hexene. It is preferred, however, that the n-hexenes be separated from the product of the etherification reaction at the same time the ethers are separated, thereby providing n-hexenes in relatively pure form for further processing in accordance with this invention.

When the etherified iso-olefins have been separated from the n-hexenes, the n-hexenes are reacted with an electrophilic compound containing reactive hydrogen. Examples of suitable electrophilic compounds containing reactive hydrogens include, but are not limited to, water, carboxylic acids, such as acetic acid, and sulfuric acid. The electrophilic compound containing reactive hydrogen is reacted with the n-hexenes, which include 1-, 2- and 3-hexene, under conditions which permit it to add to the carbon-carbon double bond in the n-hexenes. The resulting reaction product comprises a mixture of 2- and 3-hexyl isomers

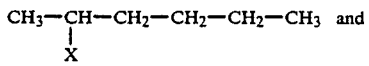

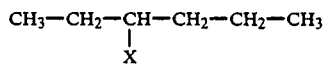

where X is the negative group e.g., —OH, —OOCCH$_3$ or HSO$_4$—) from the electrophilic compound containing reactive hydrogen.

The conditions for the addition of the electrophilic compound to the olefins are well known in the art. Generally, acid catalysis is useful. This can often be provided by the electrophilic compound itself.

The electrophilic compounds containing reactive hydrogen useful in this invention fall into two general categories. The first category comprises compounds which, after they have added to the double bonds in the hexene isomers, can be removed directly by cracking the 2- and 3-hexyl isomers. Compounds which fall into this category include water and carboxylic acids, such as formic acid, acetic acid, trimethylacetic acid, and dimethylbutyric acids. (In some cases, it may be desirable, though not necessary, to hydrolyze the electrophilic compounds in this first category, such as the carboxylic acids, to alcohols prior to cracking.) The second category of electrophilic compounds containing reactive hydrogen comprises compounds which add to the double bonds in the hexenes, but which are not readily removed from the 2- and 3-hexyl isomers by cracking, e.g., sulfuric acid. When this second category of compounds is used, the 2- and 3-hexyl isomers produced are subjected to an intermediate step, such as hydrolysis, to convert the negative group from the electrophilic compound containing reactive hydrogen (i.e., X in the above formulas) to a group, such as hydroxyl, which can be readily removed from the 2- and 3-hexyl isomers by cracking.

When the electrophilic compound containing reactive hydrogen employed is water, the 2- and 3-hexyl isomers produced will contain hydroxyl groups in the 2 and 3 positions, i.e., the product will contain 2-hexanol and 3-hexanol. Also, some of the electrophilic compounds containing reactive hydrogen which are useful in this invention can be hydrolyzed to a hydroxyl after addition to the double bond. These alcohols can be converted to xanthate groups, i.e., "2-xanthate" and "3-xanthate" compounds prepared, respectively from 2-hexanol and 3-hexanol, which can then be removed via cracking. This conversion of alcohol to xanthate can be accomplished by reacting the alcohol with carbon disulfide (CS$_2$) in the presence of base (e.g., NaOH), followed by alkylation with, e.g., methyl iodide.

As stated above, the product of the reaction of the n-hexenes and electrophilic compound containing reactive hydrogen is a mixture of 2- and 3-hexyl isomers. This mixture may be used in the subsequent cracking procedure, or, alternatively, the 2-isomers (2-hexanol, 2-xanthate, etc.) may be separated from the mixture of 2- and 3-hexyl isomers and only the 2-isomers subjected to cracking. By separating the 2-isomers in this manner, the concentration of 1-hexene in the product of the cracking procedure will be maximized.

Once the 2- and 3-hexyl isomers produced by reaction of the n-hexenes with the electrophilic compound containing reactive hydrogen contains a group which is readily removed by cracking, the mixture of 2-and 3-hexyl isomers (or the 2-hexyl isomer alone) is cracked to produce a significantly higher quantity of 1-hexene than was present in the mixture of C$_6$ olefin isomers used as the starting material. Depending upon the particular readily removable group which is present on the 2- and/or 3-hexyl isomers, removal of the group may be accomplished by simple thermal cracking or by a cracking procedure which utilizes a catalyst. For example, when acetic acid is used as the electrophilic compound containing reactive hydrogen, thermal cracking may be used. When the 2- and 3-hexyl isomers are 2- and 3-hexyl alcohols, the cracking is preferably conducted in the presence of a mildly basic metal oxide catalyst. Water is removed from each molecule to produce a mixture of 1-hexene, 2-hexene and 3-hexene which has a quantity of 1-hexene in it which is greater than the quantity of 1-hexene in the mixture of C$_6$ olefin isomers used as the starting material.

The materials useful as cracking catalysts should not be acidic or strongly basic. Acid catalysts can isomerize the 60-olefin product to internal olefins, which is undesirable. If a strongly basic catalyst is used, appreciable dehydrogenation of the alcohol would occur, which is undesirable. Thus, suitable catalysts are mildly basic metal oxides which do not cause appreciable dehydrogenation of the alcohol and which exhibit selectivity for the production of $\alpha$-olefins. While not specific to the production of 1-hexene, this general type of catalyst is discussed in an article by Burtron H. Davis entitled "Alcohol Conversion Selectivity as a Measure of the Base Strength of Metal Oxide Catalysts" in Che et al., *Adsorption and Catalysis on Oxide Surfaces* (1985); which article is incorporated by reference herein in its entirety. Examples of mildly basic metal oxides suitable as catalysts in this invention include the oxides of Y, Zr, La, In, Ce, Pr, Nd, Sm, Eu, Dy, Ho, Yb and Th.

It has been found that hydrous zirconium oxide prepared by a particular technique is an especially suitable catalyst. This catalyst is prepared by precipitating/digesting soluble ZrO(NO$_3$)$_2$ at high pH above room temperature (e.g., about 50°–75° C.), washing the resulting product thoroughly with both aqueous ammonia and water and drying exhaustively (e.g., at 80° C. or higher under vacuum for at least 16 hours). Before use, the catalyst is calcined at about 350°–650° C. This catalyst provides excellent conversion of 2-hexanol to olefin as well as excellent selectivity for $\alpha$-olefin in the product.

When the mixture of C$_6$ olefin isomers used for the starting material is derived from the Dimersol process, the above-described process can be depicted by the following general reaction scheme. This general reaction scheme is illustrative only and is not intended to limit the present invention in any way.

STEP 1

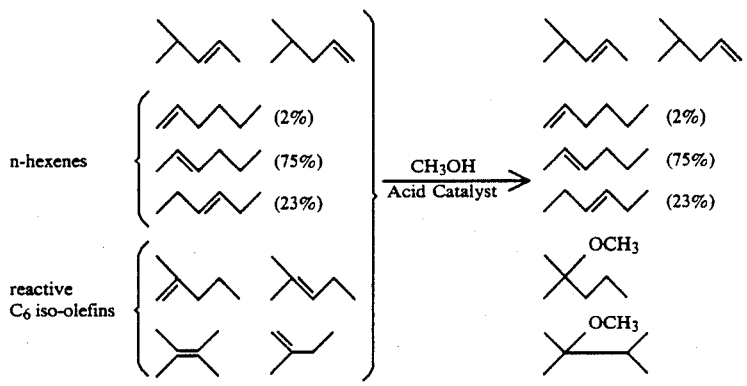

In the above Step 1, the percentages in parentheses refer to the relative amounts of 1-, 2- and 3-hexene, i.e., the weight percentages of 1-, 2- and 3-hexene based on the total weight of 1-, 2- and 3-hexene.

Assuming the 1-, 2- and 3-hexene are separated from the product of Step 1, the next step in the general reaction scheme would typically be:

STEP 2

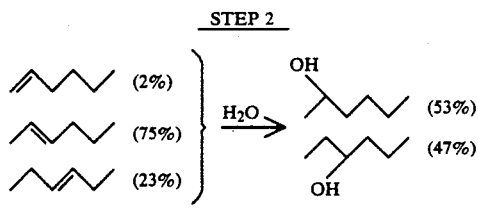

The yield of the 2-hexyl isomer (which ultimately can yield 1-hexene) in Step 2 (53 wt. % of the total product) is not substantially higher than the yield which would be expected for random addition of the water to the double bonds, i.e., about 50% of the alcohols produced would be expected to be 2-hydroxyhexane if random addition occurred. However, it has been found that the amount of 2-hexyl isomer can be increased significantly above this random level by using an electrophilic compound containing reactive hydrogen other than water. For instance, if acetic acid is used, the product contains about 63% of the 2-isomer and 37% of the 3-isomer. Using sulfuric acid as the electrophilic compound containing reactive hydrogen yields a product containing about 73% of the 2-isomer and 27% of the 3-isomer. The use of "bulky" acids, such as trimethylacetic acid or dimethylbutyric acids, should likewise increase the amount of 2-isomer in the product.

The product of Step 2 can next be "cracked" to a mixture of n-hexenes. The resulting mixture contains a quantity of 1-hexene substantially higher than the quantity present in the starting material used in Step 1.

STEP 3

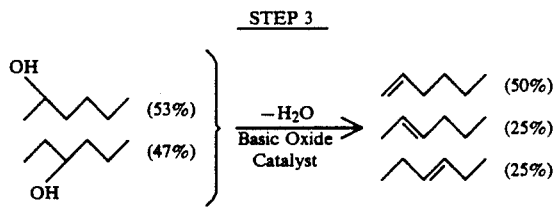

The desired product from the above reaction sequence is, of course, 1-hexene. However, it is not necessary that the 1-hexene be separated from the 2- and 3-hexene in order for it to be useful. For example, the mixture of 1-, 2- and 3-hexene can be used as a starting material for the copolymerization of 1-hexene and ethylene. Since 2- and 3-hexene will not react to copolymerize with the ethylene, they act simply as an inert diluent which can be recovered following the copolymerization of the 1-hexene and ethylene. Thus, the copolymerization also serves as a means of separating the 2- and 3-hexene from the 1-hexene.

Should it be desirable to separate the 1-hexene from the mixture of 1-, 2- and 3-hexene prior to its use, this can be accomplished by techniques such as distillation or adsorption which are well known in the art.

The processes of the present invention may be conducted either as a batch process or in a continuous manner. It is generally preferable to conduct the process in a continuous manner. The product of the cracking step will generally contain some quantity of 2- and/or 3-hexenes, and possibly some compounds which were not cracked and still contain the electrophilic group of the electrophilic compound containing reactive hydrogen (e.g., alcohols). Thus, the processes of this invention are advantageously conducted by recovering the desired product, 1-hexene, from the product of the cracking step, and recycling any remaining n-hexenes and uncracked compounds to be used as a portion of the feed for the reaction with the electrophilic compound containing active hydrogen. This may be accomplished by recycling these compounds to a point in the process where they will become part of the original starting material (which is to be etherified), or, more preferably, to a point after the etherification has taken place, but before reaction with the electrophilic compound containing reactive hydrogen. In this way the amount of 1-hexene produced from a given mixture of $C_6$ olefin isomers is maximized.

One of the principle advantages of the present invention is that it provides a process whereby 1-hexene can be produced in commercially acceptable amounts. In effect, the process of this invention starts with a mixture of n-hexenes which is low in 1-hexene and raises the quantity of 1-hexene in the mixture by converting some of the 2- and 3-hexene in the mixture to 1-hexene. For example, the mixture of propylene dimers typically resulting from the Dimersol process contains about 75% 2-hexene, about 23% 3-hexene and only about 2%

1-hexene, all percentages being by weight based on the total weight of the 1-, 2- and 3-hexene. By practicing the present invention, the amount of 1-hexene can be raised to about 50% or higher.

The present invention is further illustrated by the following examples in which all percentages are by weight unless otherwise stated.

EXAMPLE 1

The starting material for this example was the product of the dimerization of propylene by the Dimersol process, i.e., "Dimate". It was comprised of about 92% of the mixture of $C_6$ olefins indicated in Table I below, and 8% of olefins containing nine or more carbon atoms.

TABLE I

| $C_6$ Olefins in Dimate | Wt. %* |
|---|---|
| n-Hexenes | |
| cis 2-hexene | 4.0 |
| trans 2-hexene | 13.9 |
| trans 3-hexene | 5.5 |
| cis 3-hexene | 0.1 |
| 1-hexene | 0.5** |
| Methylpentenes | |
| 2-methylpentene-2 | 35.2 |
| 2-methylpentene-1 | 5.0** |
| trans 4-methylpentene-2 | 23.6 |
| cis 4-methylpentene-2 | 4.0 |
| 4-methylpentene-1 | 1.3 |
| Dimethylbutenes | |
| 2,3-dimethylbutene-2 | 4.4 |
| 2,3-dimethylbutene-1 | 2.5 |

*Weight % is based on total weight of the $C_6$ portion of the Dimate.
**Estimated 810 Grams of the above-described Dimate was treated at 50°–65° C. for 57 hours with 810 grams of methanol and 81 grams of Amberlyst 15 catalyst to etherify the reactive $C_6$ iso-olefins in the Dimate. A catalytic distillation procedure was used. The catalyst was placed in a Soxhlet extractor and the Dimate/methanol mixture was refluxed over it. In this way, the equilibrium between olefins and the higher boiling ethers was displaced toward the ethers. Under normal batch conditions, 2-methylpentene-2 would be only 73% converted to the corresponding ether, and 2,3-dimethylbutene-2 would be only 30% converted to its corresponding ether. In the present experiment, however, the 2-methylpentene-2 was 97.5% converted to ether, and the 2,3-dimethylbutene-2 was 80% converted to its corresponding ether.

The resulting product was carefully distilled to give the results shown in Table II below. The linear n-hexenes, shown as the distillation fraction cuts 15–20, were obtained in 92.5% purity. The other products, methylpentenes ("light hexenes") and ethers, were obtained in 96.3% and 98.6% purity, respectively.

TABLE II n-Hexenes and Ethers from Dimate

| Whole Product[1], % | Analysis by Gas Chromatography | Analysis by Distillation |
|---|---|---|
| Light hexenes[2] | 22 | |
| n-Hexenes | 22 | 41 |
| Other hexenes[3] | 1 | |
| Ethers[4] | 55 | 59 |

Distillation[5] Cuts

| | | Composition, % | | | |
|---|---|---|---|---|---|
| Cut | BP, °C. | MeOH | Light Hexenes | n-Hexenes | Other Hexenes | Ethers |
| 2 | 46 | 16 | 83 | 0.5 | 0.5 | — |
| 7 | 59–59.5 | — | 96.3 | 3 | 0.3 | — |
| 15–20 | 68–69.5 | — | 1.6 | 92.5 | 5.8 | — |
| 24–45 | 112–113 | 0.1 | — | — | 0.3 | 98.6 |

[1]Wt. %, methanol-free
[2]cis and trans 4-methylpentene-2 and 4-methyl-1-pentene
[3]2-methylpentene-1, 2-methylpentene-2, 2,3-dimethylbutene-1 and 2,3-dimethylbutene-2
[4]87.5/12.5 mixture of 2-methoxy-2-methylpentene and 2-methoxy-2,3-dimethylbutane
[5]Penn State packing, 20/1 reflux ratio; 2% cuts

EXAMPLES 2–4

Three more reactions were run in a manner similar to that described in Example 1. The procedure used in those reactions simulated a catalytic distillation, thereby giving a high conversion of reactive $C_6$ iso-olefins to ethers. These reactions were conducted at atmospheric pressure, so the temperature was much lower and the reaction time longer than a commercial process would be.

The differences between the procedure used for these three reactions and that used in Example 1 were:
1. The entire Dimate product, including all of the $C_{9+}$ compounds, was used as starting material.
2. The ratio of methanol to hexenes was slightly higher.
3. Less Amberlyst catalyst (about 4% of the weight of the hexenes) was used, necessitating longer reaction times.
4. The product was washed with $NaHCO_3$ and water (two times). This removed all of the methanol, whereas a little was left after the single water wash in Example 1.

Table III below indicates the extent of the conversion of some of the $C_6$ compounds in the Dimate starting material to ethers.

TABLE III

Ether Preparations

| Starting materials and reaction conditions: | Dimate[6] (2L) Methanol (2L) Amberlyst 15 (52 g)[7] Temp. 54–58° C. | | |
|---|---|---|---|
| | Example 2 | Example 3 | Example 4 |
| Reaction time, days | 7 | 11 | 16 |
| Conversion, %[8] | | | |
| 2,3-dimethylbutene-1 | 100 (3 days)[9] | 100 (4 days) | 100 (3 days) |
| 2-methylpentene-1 | 100 (7 days) | 100 (7 days) | 100 (9 days) |
| 2-methylpentene-2 | 96 | 99 | 100 (14 days) |
| 2,3-dimethylbutene-2 | 56 | 72 | 92 |
| Ether, %[10] | 43 | 43.5 | 47 |

[6]Entire Dimate product; about 79% $C_6$ compounds, 20% $C_9$ compounds, 1% $C_{12}+$ compounds
[7]Same catalyst reused in all three reactions
[8]Wt. % of indicated $C_6$ compound in Dimate starting material which was converted to ether
[9]The number in parentheses indicates the time for 100% conversion to ether
[10]Wt. % of ether in whole product In addition to the data in Table III, it was also found that the $C_{9+}$ compounds in the Dimate starting material neither reacted with the methanol, nor interfered with the reaction of the methanol and the compounds indicated in Table III. Also, the catalyst showed no sign of deactivation, even after the third reaction. The product composition and conversion level of the individual isomers were about the same as in Example 1.

A heart cut blend of the ethers prepared in Examples 2 and 3 was made for octane number testing. This blend was chosen to contain about a 85/15 ratio of the two isomeric ethers expected at full conversion. Care was taken throughout to avoid peroxide contamination by avoiding air contact during the etherification and distillation, passing the final blend of ethers over alumina, and adding 40 ppm BHT to the blend.

Infrared spectra of this ether blend were practically identical to the ether product from Example 1, except for a small band at 3500 cm$^{-1}$ which was about ten times larger for the product from Example 1. This might be associated with hydroperoxides.

Blending octane numbers for the ether blend made from the products of Examples 2 and 3 were 99 research and 91 motor.

EXAMPLE 5

This example illustrates the hydration of n-hexenes using sulfuric acid.

50 Grams of a mixture containing 1% 1-hexene, 71% 2-hexene and 28% 3-hexene was added to 93 grams of 78% sulfuric acid at 15° C. over 10 minutes while stirring and cooling. Then 60 grams of concentrated (96-97%) sulfuric acid was added over 15 minutes while keeping the temperature of the mixture at 15° C. The resulting mixture was digested at 24° C. for 1 hour. Then 288 grams of water was added at 15° C. and the intermediate sulfates which formed were hydrolyzed by heating at 80° C. for 3 hours. The resulting product contained about 70% 2-hexanol and 30% 3-hexanol. The results of this experiment and three other similar experiments are summarized below in Table IV.

EXAMPLE 6

This example illustrates the hydration of n-hexenes in a Dimate product.

A mixture of n-hexenes was prepared from the n-hexenes made in Examples 1-4. This mixture was hydrated by a procedure similar to that of Example 5 except that the starting sulfuric acid strength was about 77% and the stronger acid (137 grams) added subsequently was only about 82%. The feed blend of hexenes contained 92.4% n-hexenes and 7.6% branched hexenes. The conversion (about 75%) and alcohol isomer distribution (73% 2-hexanol and 27% 3-hexanol) were about the same as from the pure n-hexenes. The minor amount of branched hexenes in the feed mostly formed oligomers which were easily separated by distillation.

The hydrated hexenes prepared above were distilled. The results are shown in Table V below. The 2- and 3-hexanols were partially separated with the last cuts being up to about 97% 2-hexanol.

As with the procedure described in Example 5, the hydration procedure described in this example can be used in the practice of the present invention as Step 2 in the above-described general reaction scheme.

TABLE V

| | | DISTILLATION OF HEXANOLS FROM DIMATE[15] | | | | | |
|---|---|---|---|---|---|---|---|
| | | Composition, GC Area % | | | | | |
| Cut | Boiling Point, °C. | n-Hexene | "Branched Hexene" | "Branched Hexanol" | 3-Hexanol | 2-Hexanol | Oligomer |
| 1 | 62-64 | 90.4 | 8.2 | — | 0.5 | 0.9 | — |
| 4 | 68-70 | 91.2 | 6.4 | 0.1 | 0.8 | 1.5 | — |
| 8 | 138 | — | — | 1.2 | 43.6 | 55.2 | — |
| 13 | 139— | — | — | 0.2 | 41.4 | 58.2 | — |
| 18 | 139+ | — | — | — | 38 | 62 | — |
| 20-36 | 139-140.5 | | | — | 26.9 | 73.1 | — |
| 37-43 | 140.5-141 | | | | 9.7 | 90.3 | — |
| 46 | 197-199 | | | | 0.1 | 1.2 | 98.7 (C$_{12}$) |
| Bottoms | 253+ | | | | | | 100 (C$_{18}$+) |

[15]3-Ft Spinning Band, Atm. Pressure, 20/1 reflux ratio, 2% Cuts

EXAMPLE 7

This example illustrates the dehydration of hexanols.

A wide range of catalysts was tested to identify catalysts that would produce 1-hexene in high selectivities from the dehydration of 2-hexanol. One catalyst which performed well was a zirconia powder sold by Magnesium Elektron Inc. known as "SC101". This powder was pelletized and crushed to 10-30 mesh particles.

TABLE IV

| | n-HEXENE HYDRATION | | | | | | | | | |
|---|---|---|---|---|---|---|---|---|---|---|
| | Olefin Addition[11] | | H$_2$SO$_4$ Addition[12] | | Digestion | | Water | Hydrolysis | | Products[14] |
| | | | | | | | | | | GC Percent |
| Run No. | Temp. °C. | Time, Min. | Temp. °C. | Time, Min. | Temp. °C. | Time, Min. | Addition[13] Temp. °C. | Temp. °C. | Time, Min. | Color, Gardner | 2-Hexanol in Hexanols |
| 1 | 15 | 10 | 15 | 15 | 24 | 60 | 15 | 80 | 180 | 7 | 71 |
| 2 | 30 | 10 | 30 | 15 | 30 | 60 | 30 | 80 | 180 | 7.5 | 72 |
| 3 | 5 | 10 | 5 | 15 | 5 | 120 | 15 | 80 | 180 | 4 | 74 |
| 4 | 15 | 45 | 15 | 60 | 24 | 60 | 15 | 80 | 180 | 4.5 | 73 |

[11]50 grams (0.595 moles) n-hexene added to 93 grams of 78 H$_2$SO$_4$ (0.74 moles)
[12]60 grams (0.59 moles) conc. H$_2$SO$_4$
[13]288 grams water
[14]Organic layer washed with base and dried The hydration procedure described in this example can be used in the present invention as Step 2 in the above-described general reaction scheme.

Four grams were packed in a 0.5 in. diameter quartz tube and calcined in nitrogen at 550° C. for 4 hours. The feed alcohol was passed at 0.5 ml/hr over the catalyst at 300° C. in a nitrogen flow of 3 ml/min. Two blends of hexanols from Table V (cuts 20-36 and cuts 37-43)

were dehydrated by this procedure. In both cases the 2-hexanol component of the blend was about 40 to 60% converted to hexenes and a small amount of hexanones. Selectivity to olefin was about 94% and 1-hexene selectivity was about 75%. 1-Hexene can be recovered in pure form from the resulting product by careful fractional distillation.

The procedure described in this example can be used in the practice of this invention as Step 3 in the above-described general reaction scheme.

What is claimed is:

1. A process for making 1-hexene comprising:
   A. reacting a mixture of $C_6$ olefin isomers comprising (1) n-hexenes and (2) reactive $C_6$ iso-olefins with an alcohol in the presence of an acid catalyst until the reactive $C_6$ iso-olefins are etherified;
   B. separating the etherified $C_6$ iso-olefins from the product of step A;
   C. reacting the remainder of the product of step A with an electrophilic compound containing reactive hydrogen under conditions which permit the electrophilic compound containing reactive hydrogen to add to carbon-carbon double bonds; and
   D. cracking the product of step C to produce a mixture of $C_6$ olefins containing a quantity of 1-hexene greater than that in the mixture of $C_6$ olefin isomers employed in step A.

2. A process for making 1-hexene comprising:
   A. reacting a mixture of $C_6$ olefin isomers comprising (1) n-hexenes and (2) reactive $C_6$ iso-olefins with an alcohol in the presence of an acid catalyst until the reactive $C_6$ iso-olefins are etherified;
   B. separating the etherified $C_6$ iso-olefins from the product of step A;
   C. reacting the remainder of the product of step A with an electrophilic compound containing reactive hydrogen under conditions which permit the electrophilic compound containing reactive hydrogen to add to carbon-carbon double bonds;
   D. separating the 2-isomer produced in step C from the product of step C; and
   E. cracking said 2-isomers to produce a mixture of $C_6$ olefins containing a quantity of 1-hexene greater than that in the mixture of $C_6$ olefin isomers employed in step A.

3. The process of claim 1 or 2 wherein the electrophilic compound containing reactive hydrogen is selected from water and carboxylic acids.

4. The process of claim 1 or 2 further comprising separating the 1-hexene from the product of the cracking step and recycling the remainder of said product to form a portion of the material used to react with the electrophilic compound containing reactive hydrogen.

5. A process for making 1-hexene comprising:
   A. reacting a mixture of $C_6$ olefin isomers comprising (1) n-hexenes and (2) reactive $C_6$ iso-olefins with an alcohol in the presence of an acid catalyst until the reactive $C_6$ iso-olefins are etherified;
   B. separating the etherified iso-olefins from the product of step A;
   C. reacting the remainder of the product of step A with an electrophilic compound containing reactive hydrogen under conditions which permit said electrophilic compound to add to carbon-carbon double bonds, said electrophilic compound being hydrolyzable to an alcohol after addition to the carbon-carbon double bond;
   D. hydrolyzing the product of step C to produce of mixture of $C_6$ alcohols; and
   E. cracking the product of step D to produce a mixture of $C_6$ olefins containing a quantity of 1-hexene greater than that in the mixture of $C_6$ olefin isomers employed in step A.

6. A process for making 1-hexene comprising:
   A. reacting a mixture of $C_6$ olefin isomers comprising (1) n-hexenes and (2) reactive $C_6$ iso-olefins with an alcohol in the presence of an acid catalyst until the reactive $C_6$ iso-olefins are etherified;
   B. separating the etherified iso-olefins from the product of step A;
   C. reacting the remainder of the product of step A with an electrophilic compound containing reactive hydrogen under conditions which permit said electrophilic compound to add to carbon-carbon double bonds, said electrophilic compound being hydrolyzable to an alcohol after addition to the carbon-carbon double bond;
   D. hydrolyzing the product of step C to produce a mixture of $C_6$ alcohols;
   E. separating 2-hexanol from the mixture of $C_6$ alcohols produced in step D; and
   F. cracking the 2-hexanol to produce a mixture of $C_6$ olefins containing a quantity of 1-hexene greater than that in the mixture of $C_6$ olefin isomers employed in step A.

7. The process of claim 5 or 6 wherein the electrophilic compound is sulfuric acid or a carboxylic acid.

8. The process of claim 5 or 6 further comprising separating the 1-hexene from the product of the cracking step and recycling the remainder of said product to form a portion of the material used to react with the electrophilic compound.

9. A process for making 1-hexene comprising:
   A. reacting a mixture of $C_6$ olefin isomers comprising (1) n-hexenes and (2) reactive $C_6$ iso-olefins with an alcohol in the presence of an acid catalyst until the reactive $C_6$ iso-olefins are etherified;
   B. separating the etherified iso-olefins from the product of step A;
   C. reacting the remainder of the product of step A with an electrophilic reactant selected from the group consisting of water and a hydrolyzable electrophilic compound containing reactive hydrogen under conditions which permit said electrophilic reactant to add to carbon-carbon double bonds;
   D. when the electrophilic reactant employed in step C is a hydrolyzable electrophilic compound containing reactive hydrogen, hydrolyzing the product of step C to form alcohols;
   converting the alcohol produced to alkyl xanthates; and
   F. cracking the product of step E to produce a mixture of $C_6$ olefins containing a quantity of 1-hexene greater than that in the mixture of $C_6$ olefins isomers employed in step A.

10. A process for making 1-hexene comprising:
    A. reacting a mixture of $C_6$ olefin isomers comprising (1) n-hexenes and (2) reactive $C_6$ iso-olefins with an alcohol in the presence of an acid catalyst until the reactive $C_6$ iso-olefins are etherified;
    B. separating the etherified iso-olefins from the product of step A;
    C. reacting the remainder of the product of step A with an electrophilic reactant selected from the group consisting of water and a hydrolyzable electrophilic compound containing reactive hydrogen under conditions which permit the electrophilic reactant to add to carbon-carbon double bonds to produce alcohols;

D. when the electrophilic reactant employed in step C is a hydrolyzable electrophilic compound containing reactive hydrogen, hydrolyzing the product of step C to form alcohols;

E. converting the alcohols produced to alkyl xanthates;

F. separating the 2-xanthate from the product of step E; and

G. cracking the 2-xanthate to produce a mixture of $C_6$ olefins containing a quantity of 1-hexene greater than that in the mixture of $C_6$ olefins isomers employed in step A.

11. The process of claim 9 or 10 wherein the electrophilic reactant in step C is selected from water, sulfuric acid, and carboxylic acids.

12. The process of claim 9 or 10 further comprising separating the 1-hexene from the product of the cracking step and recycling the remainder of said product to form a portion of the material used to react with the electrophilic reactant.

13. The process of claim 1, 3, 5, 6, 9 or 10 wherein the cracking is conducted in the presence of a mildly basic metal oxide catalyst capable of selectively producing $\alpha$-olefins.

14. The product produced by the process of claim 1.

15. The product produced by the process of claim 5.

16. The product produced by the process of claim 9.

* * * * *